United States Patent
Weisshaupt et al.

(10) Patent No.: US 10,329,060 B2
(45) Date of Patent: Jun. 25, 2019

(54) SECURITY SEAL

(71) Applicant: AESCULAP AG, Tuttlingen (DE)

(72) Inventors: Dieter Weisshaupt, Immendingen (DE); Stefan Thomas, Tuttlingen (DE); Stefan Schuster, Villingen-Schwenningen (DE); Andreas Elisch, Schramberg (DE)

(73) Assignee: Aesculap AG (DE)

( * ) Notice: Subject to any disclaimer, the term of this patent is extended or adjusted under 35 U.S.C. 154(b) by 0 days.

(21) Appl. No.: 14/383,724

(22) PCT Filed: Mar. 12, 2013

(86) PCT No.: PCT/EP2013/054944
§ 371 (c)(1),
(2) Date: Sep. 8, 2014

(87) PCT Pub. No.: WO2013/135658
PCT Pub. Date: Sep. 19, 2013

(65) Prior Publication Data
US 2015/0014315 A1    Jan. 15, 2015

(30) Foreign Application Priority Data
Mar. 14, 2012  (DE) .................. 10 2012 004 961

(51) Int. Cl.
*B65D 50/06*   (2006.01)
*G09F 3/03*    (2006.01)
*A61L 2/26*    (2006.01)

(52) U.S. Cl.
CPC ............. *B65D 50/06* (2013.01); *A61L 2/26* (2013.01); *G09F 3/0317* (2013.01); *A61L 2202/181* (2013.01)

(58) Field of Classification Search
CPC ... B65D 73/0014; B65D 73/005; B65D 50/06
(Continued)

(56) References Cited

U.S. PATENT DOCUMENTS 3,990,131 A    11/1976  Okamura
4,712,707 A *  12/1987  Pavely ................... B65D 39/00
                                                              220/234

(Continued)

FOREIGN PATENT DOCUMENTS

DE    94 05 787 U1    6/1994

OTHER PUBLICATIONS

International Search Report for PCT/EP2013/054944 dated Jun. 4, 2013.

*Primary Examiner* — King M Chu
(74) *Attorney, Agent, or Firm* — RatnerPrestia

(57) ABSTRACT

The present invention discloses a security seal with a seal base with at least one locking projection and a seal head connected to the seal base with at least one blocking tab, whereby each blocking tab is movably connected to the seal head via at least one hinge element, together with a safety closure with a first closure part and a second closure part, which can be moved back and forth between an open position and a closed position relative to the first closure part, wherein the first closure part has a seating on which the seal base of a security seal can be engaged so that, when the second closure part is in the closed position, at least one blocking tab of the security seal at least partially overlaps the second closure part on the side of the second closure part opposite the first closure part, and additionally, a security container with a container tub, a lid and a safety closure, wherein either the first or second closure part is arranged on either the container tub or the lid, respectively.

26 Claims, 9 Drawing Sheets

(58) Field of Classification Search
USPC ......... 220/257.1, 256.1, 326, 324, 315, 323, 220/834, 833, 810; 411/508, 509
See application file for complete search history.

(56) References Cited

U.S. PATENT DOCUMENTS

| | | | |
|---|---|---|---|
| 5,651,652 A * | 7/1997 | Williams et al. | 411/508 |
| 2004/0104230 A1 | 6/2004 | Lorenz et al. | |
| 2009/0033521 A1* | 2/2009 | Ladouceur | H01H 13/705 341/22 |
| 2010/0206878 A1* | 8/2010 | Haibel | 220/321 |
| 2011/0253579 A1* | 10/2011 | Chong et al. | 206/493 |

\* cited by examiner

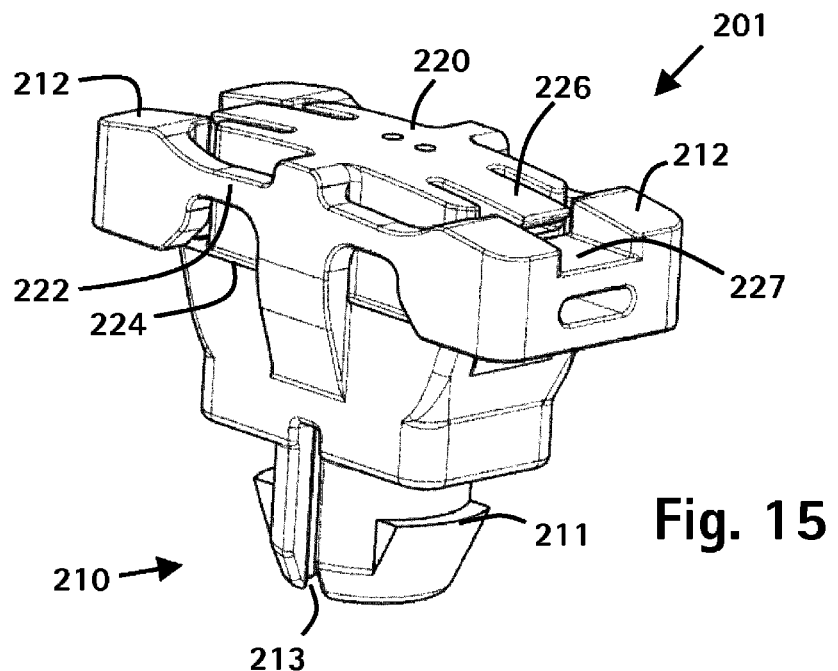
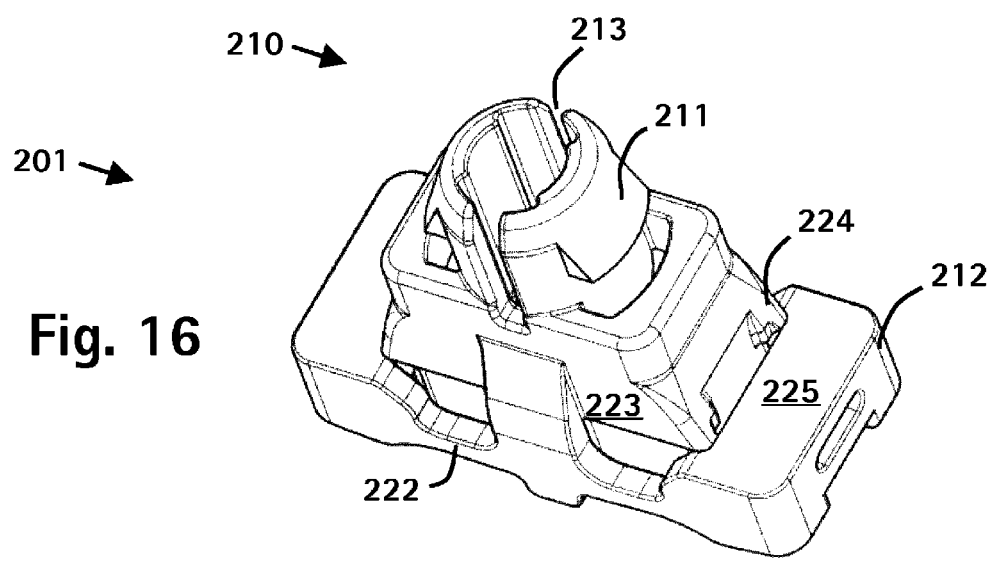

SECURITY SEAL

The present invention relates to an innovative security seal, a closure system for use with such a security seal, together with a security container and a sterilization container with such a sealing system.

Seals are used in order to be able to control whether a closure has been opened or a connection has been disconnected. Hence, for example, seals are affixed at Customs in order to ensure, for example, that sea-freight containers contain precisely those goods listed on the corresponding Customs documents. For this purpose, Customs uses wire loops, the ends of which are connected to a seal. The seal also enables checking as to whether the seal has been replaced by a new seal. In the field of medicine, for example, seals are placed on sterilization containers in order to be able to control whether such a sterilization container has already been opened following sterilization and to ensure that the instruments in the container are still sterile without fail. Various types of seal are provided for this purpose.

One very simple type of seal for sterilization containers works according to the cable tie principle, that is, a plastic loop is fed through both an eyelet on the container lid and an eyelet on the container tub and is then sealed. This type of seal is locked by its one end being provided with one or more indentations, the edges of which, pointing towards the proximal end of the loop, are tapered, while the edges pointing towards the distal end are set at a steep angle. A head with a through-hole is arranged at the other end of the loop, into which a flexible detent lug protrudes. The proximal end of the loop is introduced into the through-hole so that the detent lug snaps into the indentation. Due to the steep angle of the one edge of the indentation and the corresponding shape of the detent lug, it can be ensured that the proximal end of the loop can be easily inserted into the through-hole, while pulling on the loop does not result in the proximal end being released from the through-hole. Labelling areas or similar can also be provided on such a loop. This type of seal is intended only to be able to be opened by being destroyed i.e. by the loop being cut through at one location.

The problem with this type of seal is that it is not protected against intentional tampering. That is to say, the head of the seal can be drawn out using a thin object, and the flexible detent lug can be deformed out of the indentation, against the spring effect, at the proximal end of the seal and thus the seal can be opened without destroying it. It can even be used again afterwards and so it is no longer able to fulfil its function of securing the original condition.

As well, there is also the problem in the clinical area that a correctly opened seal, that is a destroyed seal, only loosely hangs on the two eyelets of the container and falls off easily if the lid is removed from the container tub. Since the floor of an operating theatre is considered not to be sterile, a seal which has fallen cannot simply be picked up. Since several containers are often used, frequently, as a result, several seals fall to the floor and impair the safe footing and movement and hence the concentration of the personnel.

Another safeguarding system for sterilization containers consists of a flexible card which is inserted sideways into a slot so that its free end rests in front of the locking tab. The inserted end of the card also has special recesses or holes which engage corresponding projections in the slot so that, at least with a sealed container, the card cannot be easily removed from the slot and inserted again. If the locking tab is now opened, the card bends back and then catches behind the locking tab, in its original position. If the locking tab is now closed again, the card is behind the locking tab and is no longer in front of it, and so it is indicated that the container has already been opened. The mechanism which requires exchanging the card for a subsequent sterilization process, however, is relatively complicated and hence expensive, is prone to failure and has a negative effect on the sterilization result. Moreover, this security device is also not tamper-proof. The card can be bent forwards prior to re-sealing the locking tab using a thin object so that it is then positioned in front of the locking tab again.

Another major problem with the seals and security mechanisms known to date is that it often cannot be discerned at first glance whether or not these have already been circumvented or vandalized. For example, with a seal in the form of a loop, a vandalised seal can be re-threaded into the eyelets on the container and an unwary user will not necessarily notice that the eyelet has already been vandalized and hence circumvented.

Thus, one object of the present invention is to provide a security seal in which no parts of the seal or the entire seal of the sealed closure can fall away when the seal is broken.

A further object of the present invention is to provide a security seal which prevents closing the sealed closure after the seal has been broken.

Another object of the present invention is to provide a security seal which is protected against unauthorised circumvention by actions other than opening the sealed closure.

Another object of the present invention is to provide a security seal which can only be removed if the sealed closure has already been opened. In addition, the security seal should then be able to be removed without great effort and without the need for precise manipulation.

A further object of the present invention is to provide a safety closure which has been adapted for the use of a seal according to the invention.

Another object of the present invention is to provide a security container, in particular, a sterilization container, which has a safety closure according to the invention, which been adapted for the use of a seal according to the invention.

In order to achieve these objects of the invention, a security seal according to one of claims 1 to 15, a safety closure according to one of claims 20 to 24 and a sterilization container according to one of claims 25 and 26 are provided.

In accordance with a first aspect of the present invention, a security seal has a seal base with at least one locking projection, preferably at least two locking projections, and a seal head connected to the seal base with at least one blocking tab. Here, each blocking tab is movably connected to the seal head via at least one hinge element.

In this manner, the security seal can be mounted and fastened in a corresponding seating in a first closure. The locking projection guarantees the quick, straightforward attachment of the security seal on to a corresponding seating. Here, the blocking tab locks the second closure part so that the closure cannot be opened. In most cases, this will be a closure where one locking piece is removed perpendicular to the other locking piece (i.e. the locking pieces remain essentially parallel with one another) or by pivoting around the other locking piece (i.e. by rotating around an axis of rotation, which is at the level of the closure) in order to open the closure. It is also possible, however, to arrange this security seal on a lock, where one closure part moves and/or twists against the other in the closure section (the closure parts remain parallel to one another; twisting, where required, is around an axis, which is perpendicular to the closure section). A lug can also be arranged on the blocking tab, which engages the closure part on which the security seal is not mounted. This tab engages a corresponding indentation in the closure part in which the blocking tab engages. If this is now moved, the tab is disengaged from the indentation with the aid of the hinge element.

According to one advantageous further development of the first aspect of the present invention, the at least one hinge element can be deformed at least to some extent.

By this means, it can be ensured that the blocking tab can no longer completely return to its original position after the respective closure has been opened. A plastic deformation might be able to be partially undone, but it is not possible to undo this completely. At least visible deformations will remain on the surfaces of the hinge element or hinge elements in the area of the bending. Thus, it can be seen on the seal that the associated closure has already been opened at least once. Hence, due to its first use, the seal has been voided. The plastic deformation is particularly advantageous in counteracting deliberate tampering with the seal or with the sealed closure. It is also advantageous if the deformation is not exclusively plastic but also includes an elastic part. In this way, one part of the security tab can initially be pushed out of its trajectory, through the blocked closure part, on opening the associated closure and can then return to its trajectory.

By moving the closure elements relatively within the closure section or perpendicularly to the longitudinal axis of the security seal to open the closure and with a blocking tab with a lug to engage in the blocked closure part, the interaction of the blocking tab with the trajectory of the closure part is outlined as follows. The direction of movement of the blocked closure part relative to the security seal and hence to the other closure part is essentially parallel to the direction of the extension of the hinge element in its original state. Oblique contact surfaces on the closure part and on the blocking tab provide that, when the closure parts are removed from one another, the lug on the blocking tab is easily taken out of the indentation in a direction essentially perpendicular to the direction of the extension of the hinge element, wherein oblique in this connection means that the angle between these surfaces and the direction of movement is not all that great, for example 45°±10° (not an absolute boundary). Here, the hinge element is deformed elastically and plastically. If the previously blocked closure part is completely removed, the blocking tab straightens back elastically, so that only the plastic deformation remains. If an attempt is now made to insert the previously blocked closure part into the closed position, then at least both surfaces of the lug on the blocking tab of the previously blocked component collide with the surfaces, which are each arranged on the sides of the respective component to the oblique contact surface in the direction of movement. If these surfaces now assume an essentially perpendicular position to the direction of movement, then the blocking tab does not move out of the way and hence prevents the previously blocked locking tab from returning to its initial position or blocked position.

In the relative movement of the closure elements out of the closure section to open the closure or parallel to the longitudinal axis of the security seal to open the closure, the interaction of the blocking tab with the trajectory of the closure part is outlined as follows. The blocking tab blocks the blocked closure part by overlapping this at least partially in the direction of movement. If the closure part is now moved out of the closed position, that is, raised or pivoted, the blocked closure part, with elastic and plastic deformation of the at least one hinge element, pushes the blocking tab out of the trajectory of the closure part. If the closure part is removed completely from the security seal, the blocking tab returns into the trajectory of the previously blocked closure part to such an extent that that the induced elastic deformation is undone. In this case, the direction of the extension of the at least one hinge element is essentially perpendicular to the direction of movement of the closure part, at least in the area in which there is contact between the security seal and the blocked closure part. If the previously blocked closure part now attempts to return to the closed position, it comes into contact with the blocking tab. By means of a suitable design of the corresponding contact surfaces, the blocking tab can now be prevented from moving out of the way of the previously blocked closure part and hence its trajectory is clear. In fact, the security seal can be designed such that the contact between the blocking tab and the closure part results in the blocking tab again being pushed into the trajectory of the closure part. An end stop or contact surface preventing the blocking tab from being pulled out of the trajectory in the opposite direction of the first deformation can also be arranged on the security seal. Typically, however, this is already guaranteed by the seal head or the seal base itself or by positioning the blocking tab on an upper surface of the first closure part.

According to one advantageous further development of the first aspect of the present invention, the security seal is formed as one piece, preferably from plastic. A one-piece security seal has the advantage that no assembly steps are required. Plastic is a particularly suitable material since this can easily be formed into the desired shape, for example by injection molding, and since certain undercuts can also be formed on the security seal in a casting process with forced deformation. Alternatively, the security seal can also be made from metal or a composite material. If the security seal is now made in one piece, the at least one hinge element is twisted with a displacement of the blocking tab. Here, at least one part of the blocking tab is plastically deformed, so that, in a security seal made from plastic, so-called stress whitening occurs. This plastic deformation ensures that the blocking tab can no longer be completely brought back into its original position. With suitably selected material characteristics In a security seal made from plastic, the blocking tab can also be prevented from snapping or tearing off the security seal on bending the least one hinge element. Here, the voided security seal itself is a single piece and is not destroyed and broken into several parts so that no part of the security seal comes off and must then be collected.

According to one particularly advantageous further development of the first aspect of the present invention, the security seal has two, preferably radially opposing, blocking tabs. Here, the seal head is more or less butterfly-shaped. A seal formed in this way is particularly suitable for closures in which the seal is inserted into a through-hole provided in a first closure part. If the seal is closed again after opening the seal and consequently bending both blocking tabs, the blocking tabs come into contact with the opposing edges of the through-hole. Due to the geometry of the security seal and the lugs, the security seal becomes wedged in the through-hole so that it can thus be ensured that the closure can no longer be closed until the security seal is removed from the closure.

According to an advantageous development of the first aspect of the present invention, two hinge elements are arranged on each blocking tab of the security seal, preferably on the sides of the seal head. Each blocking tab is stably and securely connected to two hinge elements. Thus, the blocking tab opposite the seal head can also be prevented from twisting around an axis parallel to the hinge element. If the hinge elements are arranged on the side of the seal head, the hinge elements can be designed to be longer so that the corresponding blocking tab has a trajectory with a greater radius of curvature. This results in a voided seal being more easily recognized, even where the user takes little notice, since the blocking tab takes up a position further removed from its original position.

According to one particularly advantageous further development of the first aspect of the present invention, the seal base has an essentially circular cross-section. This makes a security seal possible, which can be inserted or plugged linearly into a corresponding seal base seating and can then be rotated around the longitudinal axis of the seal if the seal is opened, in order to raise the undercut for the locking projection with the seal base seating and to remove the seal from the seal base seating. Alternatively, the seal base can also be rectangular. Then the security seal can be displaced, for example, perpendicularly to the longitudinal axis of the seal in order to raise the undercut between the locking projection and the seating.

According to a further advantageous development of the first aspect of the present invention, each blocking tab protrudes at least partially radially towards the seal base. Thus, the lateral surface of the seal base can be in contact with the edge of the seal base seating and hence guarantee a secure support for the security seal in the seating.

According to an advantageous further development of the first aspect of the present invention, the at least one locking projection protrudes radially outwards from the seal base. This type of security seal, if the seal base has a circular cross-section, requires only a circular hole for the seating with at least one radial widening, through which the at least one locking projection passes so that the security seal can be easily removed from the seating when required. For logical reasons, the number of radial recesses is equivalent to at least the number of locking projections which protrude outwards. Radial widening in this context means that the diameter of the seating in the area of the widening is greater than at a point at which there is no radial winding.

According to one advantageous further development of the first aspect of the present invention, at least one radial projection or indentation is formed on the seal head or on the seal base, with which the side of at least one blocking tab facing the seal base is in contact. This radial projection prevents the blocking tab from inadvertently being deformed in the wrong direction and hence inadvertently voiding the security seal. If the security seal is introduced into the seating of an open seal and the seal is then closed, then the at least one blocking tab will be deformed towards the seal base. This deformation would result in a plastic deformation in the at least one hinge element and hence the seal would be voided. Such a seal could no longer be used. If, however, the blocking tab is in contact with a projection in this trajectory, the plastic deformation of the hinge element due to moving in this direction is prevented. Hence, accidental voiding of the seal is also prevented by this means.

According to one advantageous further development of the first aspect of the present invention, the at least one locking projection on the seal base is elastically mounted and protrudes inwards in a radial direction. In such a case, a recess is not suitable as a seating, but a mushroom-head lug. Here, the at least one elastic locking projection encloses the mushroom head and forms an undercut with this. Preferably, more than one elastic locking projection is provided. The mushroom shape, however, is only one example of a seating lug. It is only important that the lug has at least one surface which makes possible an undercut with the least one locking projection of the security seal. Likewise, the shape of the surface of the lug facing the security seal is not important. Preferably, this is essentially circular and curved approximately hemispherically. It can, however, also be designed to be flat and have a circular shape with a number of notches or, for example, essentially in the shape of a cross.

According to a particularly advantageous further development of the first aspect of the present invention, a number of locking projections are provided, which are preferably arranged around the seal base, at the same angular distance to one another wherein preferably an even number of locking projections is provided, in particular, two, four or six locking projections. On the one hand, this type of design results in a symmetrical security seal or a symmetrical seal base, so that the user does not have to pay so much attention to inserting the security seal into the seating in the correct position. Here, the multiple locking projections enable the security seal to be attached to the corresponding seating particularly easily and, at the same time, securely and free of play.

According to a further particularly advantageous further development of the first aspect of the present invention, at least one elastic spring tab is arranged at the seal head, which protrudes radially over the inner edge of a blocking tab. If the blocking tab in this type of seal is moved out of its original position over the elastic spring tab, this spring tab then helps to prevent the return of the blocking tab into its original position. An elastic spring shackle of this type is particularly advantageously designed if it is at least partially in contact with the seal head or the seal base on the side facing the seal base. In this case, the elastic compression length has a variously effective bending length in the opposite direction of movement to that of the associated blocking tab. If the blocking tab is deformed out of its original position, it thereby bends the elastic spring shackle open. The spring shackle can deform freely in this direction and exerts only a relatively slight resistance to the blocking tab. The bending radius of the elastic spring shackle in this direction is relatively large. In the opposite direction, the elastic spring shackle is in contact with a part of the security seal. This shortens the effective length of the spring shackle for bending in this direction and reduces the bending radius of the spring shackle. This results in the spring shackle being substantially more rigid in this direction than in the opposite direction and hence the spring shackle exerts a significantly greater resistance to the blocking tab. With a suitably selected geometry of the elastic spring shackle, the resistance to returning exerted on the corresponding blocking tab can become so great that the blocking tab is essentially precluded from returning to its original position.

According to an advantageous further development of the first aspect of the present invention, the at least one elastic spring tab is mounted on the other side of the seal head and preferably centrally. In this way, the effective compression length of the elastic spring shackle to deflect the blocking tab from the seal base can be increased. At the same time, this spring shackle can be in contact with the seal head over its entire radius, whereby the effective compression length for a deformation towards the seal base remains small since only the length from the outer edge of the seal head, where the spring shackle is in contact on the seal head, to the free end of the spring shackle is significant for this purpose. It is also conceivable that a spring shackle is mounted on the seal head, in the area of the opposing edge of the seal head over which it protrudes.

According to an advantageous further development of the first aspect of the present invention, at least one radially protruding second locking projection is provided on the lateral surface of the seal head and a lug is arranged on at least one blocking tab so that this is located radially opposite the second locking projection and in an axial direction, further towards the seal base in comparison with the second locking projection. According to this design, the lug slides over the second locking projection where the blocking tab is deformed or moved from its original position, wherein the lug is pushed radially outwards by the second locking projection and/or the second locking projection is pushed radially inwards by the lug. This is facilitated if the corresponding sliding surfaces are smooth and do not adopt too obtuse an angle to the longitudinal axis of the security seal. If the lug has now slid past the second locking projection, this now engages the second locking projection. This reliably prevents the blocking tab from returning to its original position.

According to an advantageous further development of the first aspect of the present invention, at least the lug or the second locking projection is elastically flexible. In this way, with little exertion of force, the lug can slide past the second locking projection. With a non-flexible lug and a second locking projection, however, the required radial displacement can also be provided by the at least one hinge element, which is accordingly elastically extended.

According to a second aspect of the present invention, a safety closure has a first closure part and a second closure part, which can be moved back and forth between an open position and a closed position. Here, the first closure part has a seating into which the seal base of a security seal according to the preceding aspect and its advantageous developments can be engaged so that, when the second closure part is in the closed position, at least one blocking tab of the security seal at least partially overlaps the second closure part on the side of the second closure part opposing the first closure part.

Thus, a safety closure can be provided, with which it is reliably indicated whether the closure has already been opened once if a security seal has been set in the corresponding seating. This cannot be removed without deforming and moving the blocking tab out of its original position due to overlapping the blocking tab of the security seal with the second closure part. Where the second closure part is moved relative to the first closure part at the level of the closure, the blocking tab of the security seal has a lug in the direction of the seal base which engages in an indentation or a through-hole in the second closure part.

According to an advantageous further development of the second aspect of the present invention, the second closure part has a recess and/or a through-hole, and here, the seal base can be inserted and engaged in the closed position of the second closure part in the seal base seating of the first closure part. This design is particularly advantageous since a form closure can thus be produced between the security seal and the second closure part or both closure parts so that the security seal cannot be turned, tilted and/or shifted at the level of the closure in order to remove the security seal from its seating once the closure has been closed.

According to an advantageous further development of the second aspect of the present invention, when the second closure part is in the closed position, the seal base of the security seal can be engaged in the seal base seating of the first closure part so that the security seal is interlocked with the second closure part so that the security seal is essentially clamped immovably with respect to the first closure part, and, in particular, cannot be turned, tilted and/or shifted, whereas the security seal can be moved, in particular, turned, tilted and/or shifted with respect to the first closure part, when the second closure part is in the open position. This aspect is particularly advantageous since only the form closure between the second closure part and the security seal is produced so that the first closure part can be freely designed.

According to an advantageous further development of the second aspect of the present invention, the seating has at least one recess on the first closure part, preferably with an essentially rotationally symmetrical section with at least one outward radial widening, into which a seal base of a security seal can be inserted. In this way, a closure for a security seal can be created which can be released from the closure by turning the seal around its longitudinal axis. Here, once installed, the rotationally symmetrical section of the seating forms the snap-on connection with the least one locking projection of the security seal. To release the undercut, the at least one locking projection is turned into the position of the at least one radial widening.

According to an advantageous further development of the second aspect of the present invention, the seating on the first closure part has an essentially annular recess with at least one outward and/or inward radial widening, into which the at least one locking projection can be inserted. In this way, manufacturing the seating of the seal is particularly simple and inexpensive and at the same time the seal is less susceptible to damage. Here, it should be noted that the closure elements are not always handled very carefully and, for example, when used on sterilization containers, must also be able to withstand the sterilization process.

In accordance with another advantageous further development of the second aspect of the present invention, the seating on the first closure part is a mushroom-shaped projection on which a seal base of a security seal can be placed. This type of seating enables the security seal to be placed on the mushroom-shaped projection from above and for the same to be disengaged from the projection by tilting the security seal towards the projection and then pulling the seal from the projection. Thereby, at least one elastic locking projection is bent outward when the seal is tilted towards the projection, which is facilitated by a favorable leverage.

In accordance with another advantageous further development of the second aspect of the present invention, the safety closure has an additional known closing mechanism, in particular, a snap-in mechanism, with which the second closure part can be locked onto the first closure part. Thus, the safety closure is not responsible for the actual closure and/or locking of the first and second closure part, but only serves to fulfil the security aspect of the safety closure. That is, the safety closure is present to indicate with certainty that it has not yet been opened after the security seal was affixed, i.e. it is still locked. These can be individualised, for example by consecutive numbering, a signature, lettering, etc., in order to identify whether the security seals have been exchanged.

According to a third aspect of the present invention, a security container comprises a container tub, a lid and a safety closure according to the second aspect of the present invention and its advantageous embodiment, wherein either the first or the second closure part is arranged on either the tub or the lid respectively. In this way, for example, a container can be provided, the lid of which is attached to one side of the tub by a hinge. In this case, a safety closure arranged on another side, preferably the opposite side of the tub, to which the lid is hinged, is adequate. A container can also be designed, however, the lid of which is not hinged to the tub. In order to guarantee a reliable closure, two safety closures should preferably be provided on opposite sides of the container.

According to an advantageous further development of the third aspect of the present invention, the first closure part or the second closure part is arranged on a locking tab, which is accordingly swivel-mounted on the container tub and/or the lid. In this way, a closure can be provided in which the second closure part pivots towards the first closure part. This design makes a particularly simple structure of the safety closure possible and the security seal with, at the same time, a very high level of security. Advantageously, a tilted locking tab suggests an improper closure and, where the safety closure has been closed correctly, the locking tab is positioned vertically, for example, or horizontally. The tilted position of the locking tab is also more easily recognized by the unwary user, whereby the level of security of the security container is increased.

According to a fourth aspect of the present invention, a sterilization container has a container tub with at least a first closure part, which has a recess with two opposing curved contact surfaces formed on two curved sections, between which two radial recesses are arranged. This recess is aligned to receive a seal base of a security seal, which has an essentially circular cross-section and two locking projections projecting outwards and which can be inserted into the recess in an axial direction, so that the locking projections create a locking undercut with the curved sections and a lateral surface of the seal base is partially seated on the contact surface. The recess is also aligned so that the snap-on connection between the locking projections and the curved sections can be lifted off by turning the security seal around its longitudinal axis through roughly 90°, so that the security seal can be removed from the recess. The sterilization container also has a container lid, which has at least one locking tab, which is swivel-amounted to this so that it can be moved back and forth from an open position to a closed position, and has a second closure part, which has a through-hole, which has an essentially non-rotationally symmetrical cross-section and is aligned to interlock with a seal head of the security seal in the direction of rotation so that moving the locking tab in the direction of the open position relative to the security seal results in at least one blocking tab arranged on the seal head of the security seal being positioned on at least one part of the edge of the through-hole and continued movement of the blocking tab in this direction results in at least partial plastic deformation of the at least one blocking tab so that the through-hole of the locking tab can be guided over the seal head.

Thus, a sterilization container can be provided, for which, thanks to the security seal, it can be guaranteed that the sterilization container has not been opened after sterilization, so long as the security seal his intact. This can also still be easily and reliably determined, even where little attention is paid.

According to an advantageous further development of the fourth aspect of the present invention, an additional locking or closure mechanism is arranged between the locking tab and the first closure part so that the safety closure is essentially force-free when the locking tab is in the closed position. In this way, the safety closure only serves to guarantee the closed position since the installation of the security seal. The actual closure is achieved by other lock components, which are arranged on a separate lock or on the safety closure. If the safety closure and hence the security seal remain force-free, the security seal cannot be damaged if the sterilizing container is lifted by the container lid, for example.

Further advantages and characteristics of the invention will be apparent to the expert in the attached figures and the detailed description of the exemplary embodiments.

FIG. 15 shows a perspective view of a security seal in accordance with a third exemplary embodiment of the present invention, in a non-voided state;

FIG. 16 shows another perspective view of a security seal in accordance with the third exemplary embodiment of the present invention, in a non-voided state;

Exemplary embodiments of the present invention are described in detail in the following, with reference to the figures.

A first exemplary embodiment of the present invention is described in the following with reference to FIGS. 1 to 7.

Figure 1:
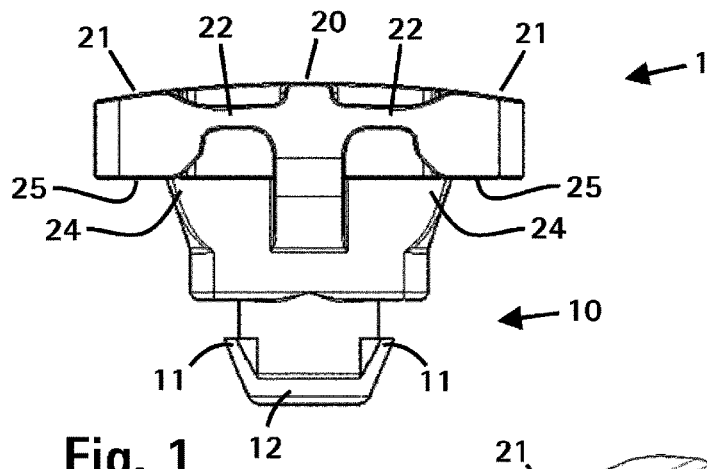
FIG. 1 shows a lateral view of a security seal in accordance with a first exemplary embodiment of the present invention, in a non-voided state.
Figure 2:
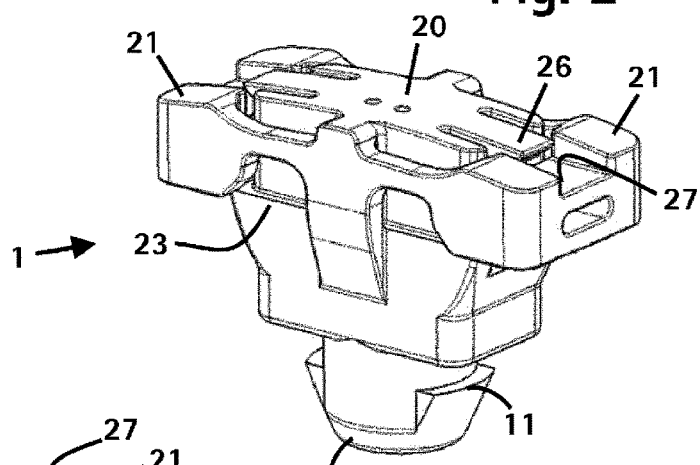
FIG. 2 shows a perspective view of a security seal in accordance with the first exemplary embodiment of the present invention, in a non-voided state.
Figure 3:
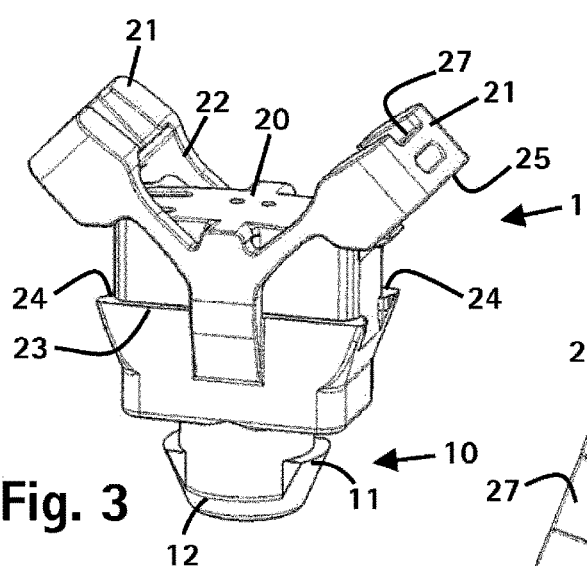
FIG. 3 shows a perspective view of a security seal in accordance with the first exemplary embodiment of the present invention, in the voided state.

The security seal 1 according to the first exemplary embodiment has a seal base 10 with two locking projections 11 and a seal head 20. The security seal 1 also has two blocking tabs 21, wherein each blocking tab 21 is movably connected to the seal head 20 via two hinge elements 22 (of which only one of each is depicted in FIG. 1). The entire security seal 1 is manufactured from plastic by means of an injection molding technique. The hinge elements 22 are plastically deformable, that is, so-called stress whitening occurs in the hinge elements 22 when the hinge elements 22 are bent beyond a certain degree. The degree of bending or deforming from which the stress whitening and hence the plastic deformation of the hinge elements 22 occurs depends on the height and width of the hinge elements 22 and on its material properties, that is, in this exemplary embodiment, the material properties of the selected plastic.

As can be seen in FIGS. 1 to 4, the two blocking tabs 21 in this exemplary embodiment are arranged radially opposite; in this exemplary embodiment, the entire security seal 1 is, in fact, mirror-symmetrical, which is generally an advantageous design for a security seal 1 according to the invention. The hinge elements 22, by which the blocking tabs 21 are held onto the seal head 20, are arranged laterally on the seal head. The seal base 10 has an essentially circular cross-section. In this exemplary embodiment, a cylindrical projection 12, on which the two locking projections 11 are arranged, projecting radially outwards, extends from the seal head 20. The locking projections 11 extend in the same directions, towards the seal base 10, as the blocking tabs 21 extend towards the seal head 20.

Figure 4:
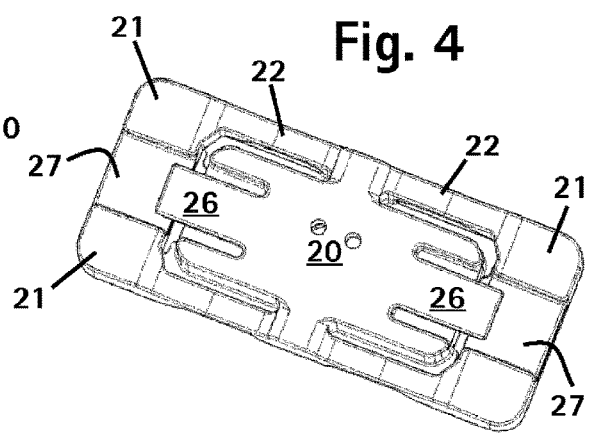
FIG. 4 shows a perspective view of a security seal in accordance with the first exemplary embodiment of the present invention, in a non-voided state.
Figure 5:
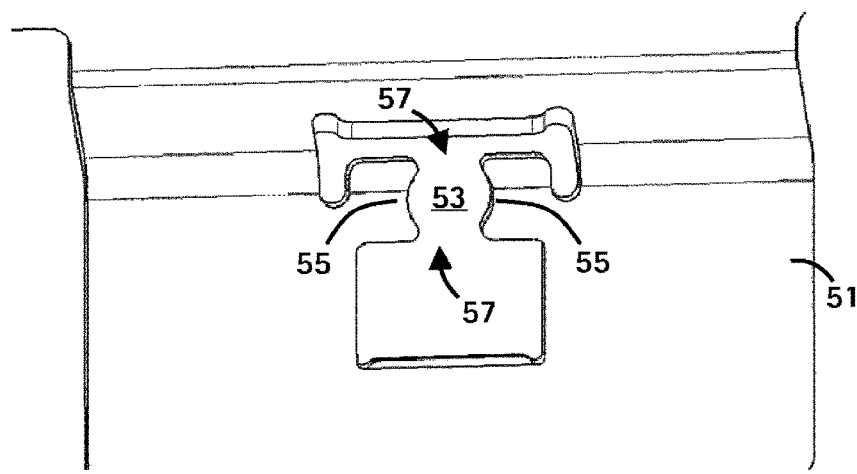
FIG. 5 shows a perspective view of a seating for a security seal in accordance with the first exemplary embodiment of the present invention.
Figure 6A:
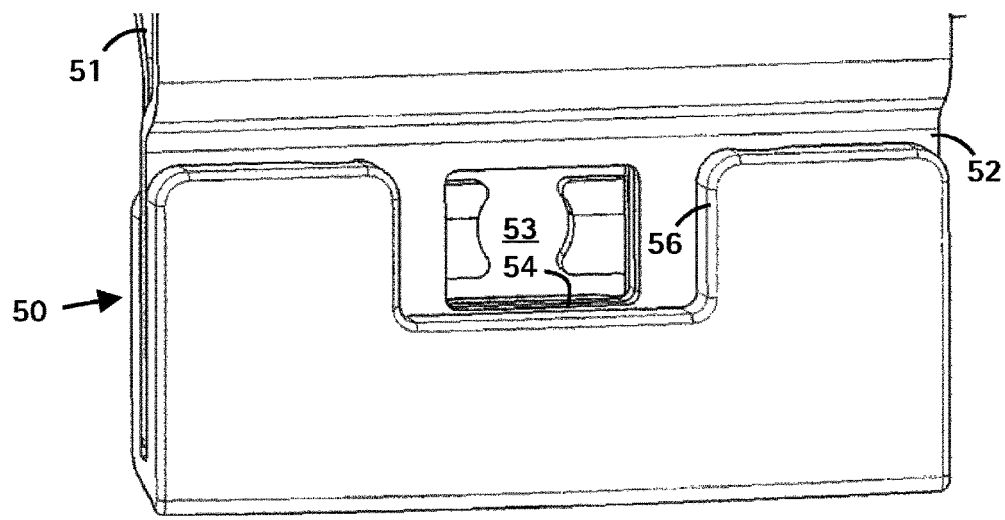
FIG. 6A shows a perspective view of a safety closure in accordance with the first exemplary embodiment of the present invention.
Figure 6B:
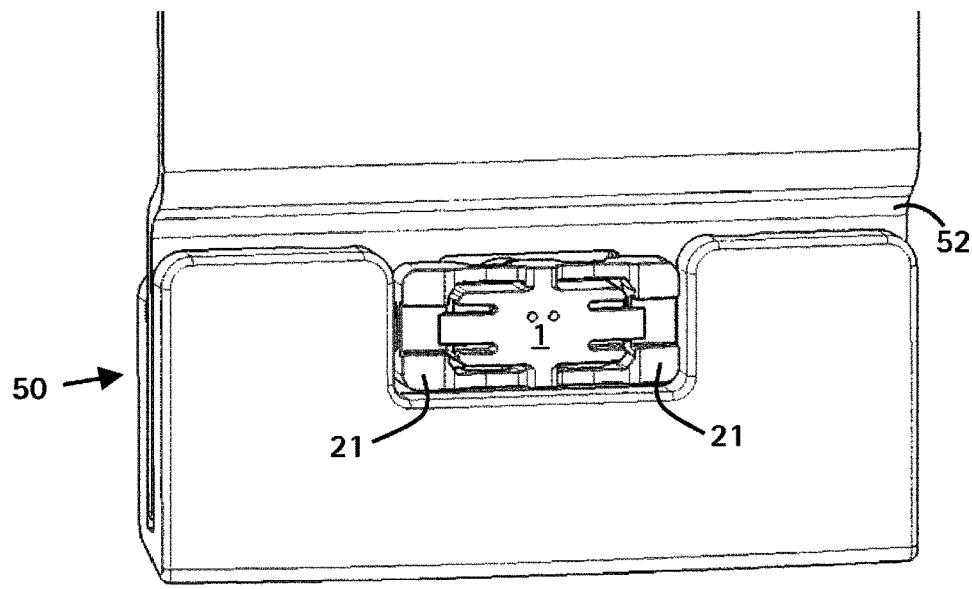
FIG. 6B shows a perspective view of the safety closure in accordance with the first exemplary embodiment of the present invention, with the security seal.
Figure 6C:
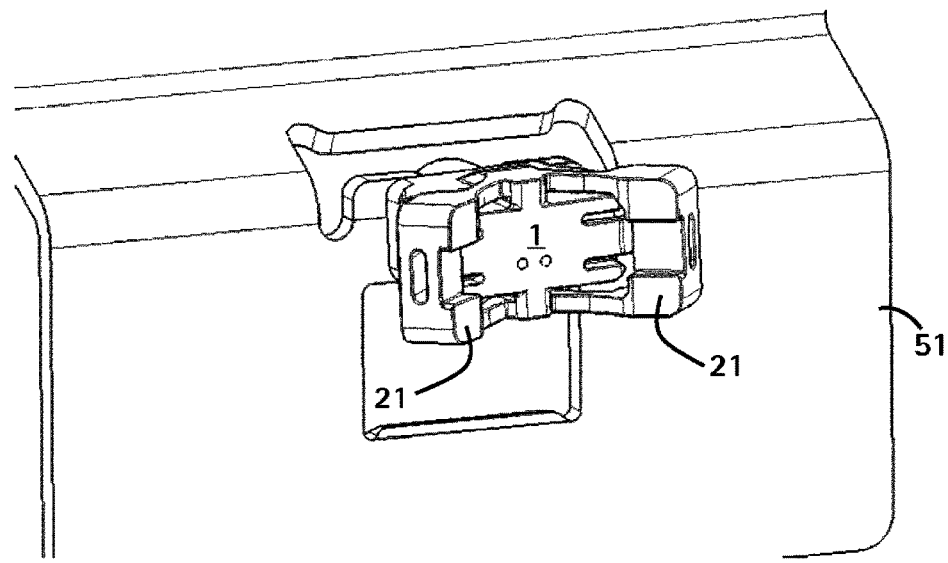
FIG. 6C shows a perspective view of a part of the safety closure in accordance with the first exemplary embodiment of the present invention, with the voided security seal.
Figure 7A:
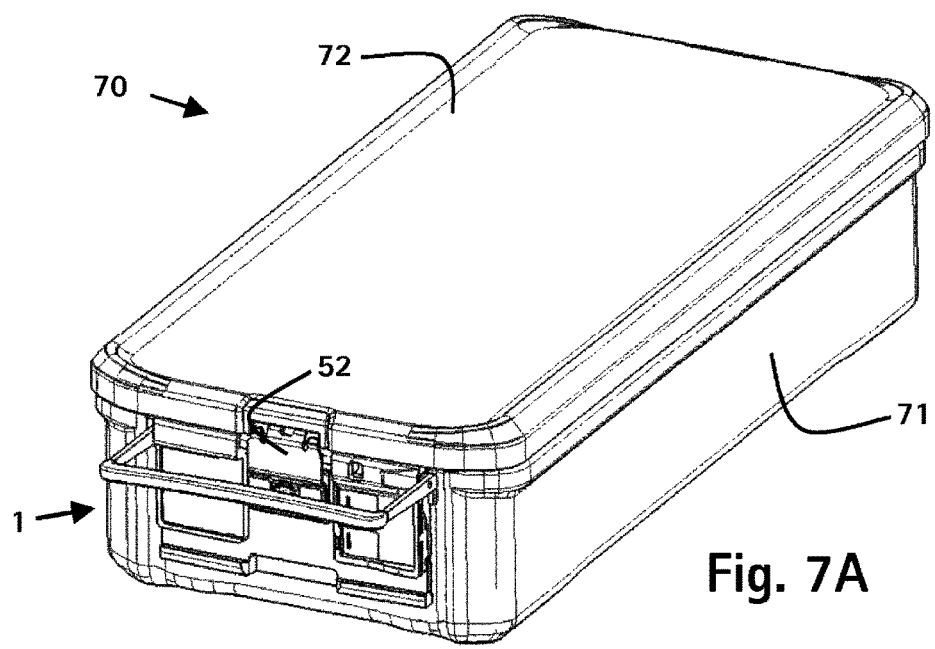
FIG. 7A shows an isometric view of a sterilization container with a safety closure and a security seal in accordance with the first exemplary embodiment of the present invention.
Figure 7B:
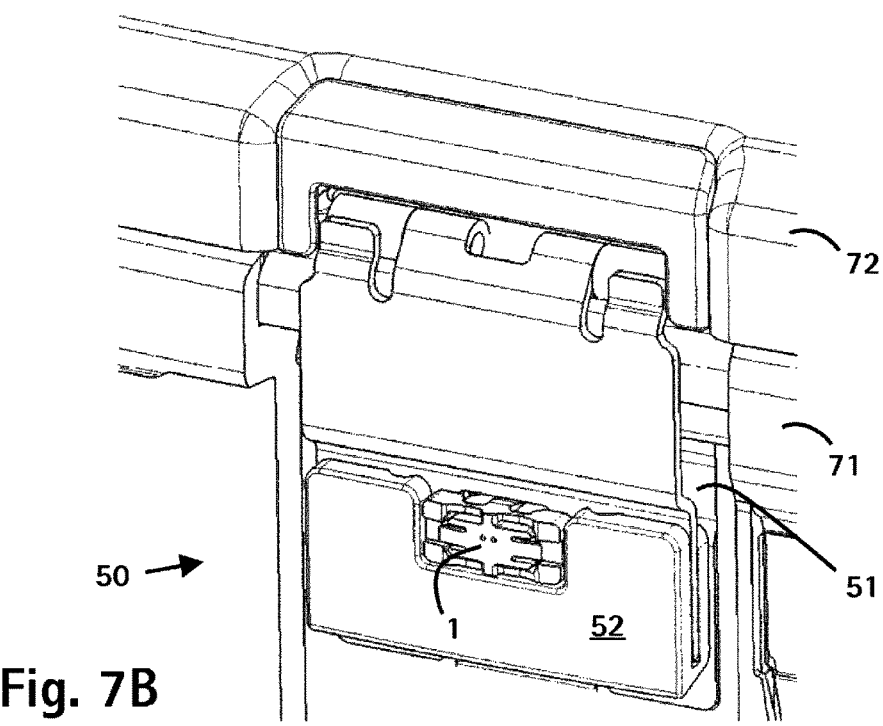
FIG. 7B shows an enlarged detail of FIG. 7A.
Figure 8:
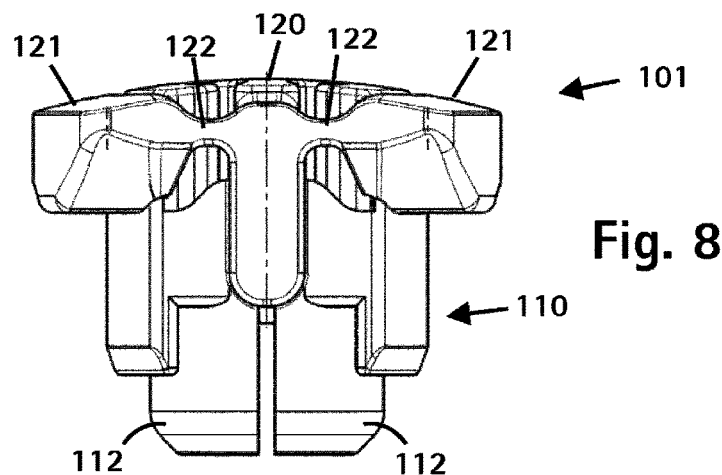
FIG. 8 shows a lateral view of a security seal in accordance with a second exemplary embodiment of the present invention, in a non-voided state.
Figure 9:
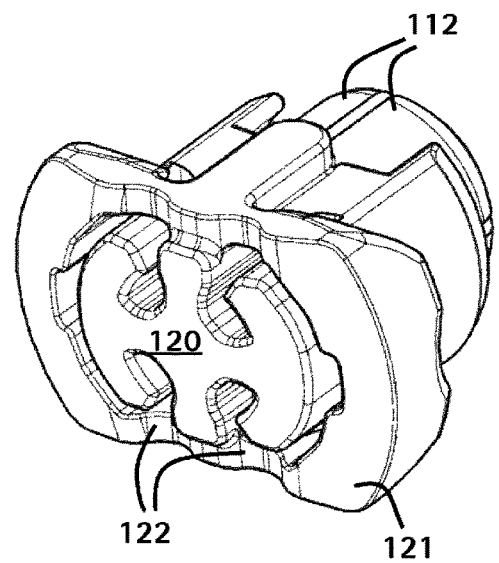
FIG. 9 shows a perspective view of a security seal in accordance with the second exemplary embodiment of the present invention, in a non-voided state.
Figure 10:
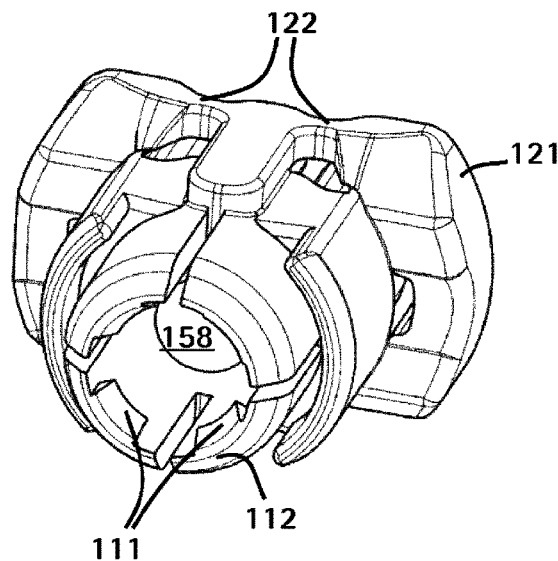
FIG. 10 shows another perspective view of a security seal in accordance with the second exemplary embodiment of the present invention, in a non-voided state.

The seal head 20 has an essentially rectangular cross-section and the two blocking tabs 21 and the associated hinge elements 22 also have an essentially rectangular cross-section, as can be seen particularly in FIG. 4 and FIG. 6B. Both the blocking tabs 21 project radially, i.e. laterally in this exemplary embodiment, towards the seal base 10 and the seal head 20.

In addition, two projections 23 are arranged on the seal head 20, projecting laterally from the seal head 20. These two projections 23 extend along the longer side of the essentially rectangular seal head 20 and together form four supporting surfaces 24 on which the sides 25 of the two blocking tabs 21 facing the seal base 10 each rest.

As depicted in FIG. 4, the security seal 1 according to this exemplary embodiment has two elastic spring tabs 26. These elastic spring tabs 26 are arranged or formed centrally on the upper surface of the seal head 20 and project radially from the seal head 20 over the edge of the respective blocking tab 21. This means that the free distal ends of each elastic spring tab 26 respectively overlap a part of the upper surface, i.e. the side facing the seal base 10, of a blocking tab 21. Both blocking tabs 21 in these overlapping areas also have recesses 27 so that the upper surfaces of the elastic spring tabs 26, the upper surface of the seal head 20 and the upper surface of the two blocking tabs 21 essentially form a single surface. This results in a particularly comfortable feel of the security seal 1 when this is placed in the corresponding seal base seating and a harmonious appearance of the security seal 1.

Otherwise, the two elastic spring tabs 26 are only attached to the seal head 20 at their proximal ends, in the central section of the same. The underside of the spring tabs 26, that is, the sides of the spring tabs 26 facing the seal base 10, are not attached to the seal head 20. These sides are either in contact with the seal head 20 or, in fact, a gap is formed between the spring tabs 26 and the seal head 20. Thus, the elastic spring tabs 26 can actually be easily bent upwards by the seal head 20, that is, away from the motor seal base 10, in order to allow them to bypass the blocking tabs 21. On the other hand, it is difficult to bend these elastic spring tabs 26 in the opposite direction in order to allow the blocking tabs 21 to pass in the opposite direction, namely in trying to return these to their original position. This is because the undersides of the spring tabs 26 are supported by one part of the upper surface of the seal head 20 so the that elastic spring tabs 26, bending in both directions as described above, have a different effective length.

A safety closure 50 in accordance with the first exemplary embodiment, with a first closure part 51 and a second closure part 52, is depicted in FIGS. 6 and 6A to 6C. This safety closure 50 has been adapted for use in conjunction with the security seal 1 in accordance with the first exemplary embodiment. The security seal 1 in accordance with the first exemplary embodiment and the safety closure 50 in accordance with the first exemplary embodiment work together as a key and an associated lock or a plug and its corresponding socket.

In the safety closure 50 in accordance with this exemplary embodiment, the second closure part 52 can be moved relative to the first closure part 51, between an open position and the closed position, due to being able to be pivoted in this direction. The first closure part 51 has a seating 53, into which the seal base 10 of the security seal 1 can be engaged. The security seal 1, in particular, can also be engaged in the seating 53 when the second closure part 52 is in the closed position, i.e. when the second closure part 52 overlaps the first closure part 51.

The seating 53 is designed so that it has sections which can create undercuts with the locking projections 11 of the seal base 10 of the security seal 1. In this exemplary embodiment, these are the two curved sections 55 delimiting the seating at the sides. Two open sections 57 are formed between the two curved or arc-shaped sections 55. These open sections 57 are formed so that they cannot form undercuts with the locking projections 11 of the security seal 1. If the security seal 1 is to be removed from the seating 53, the security seal must be turned far enough around its axis relative to the seating 53 to position the locking projections 11 of the security seal 1 in the open sections 57. In this position, the security seal 1 can be pulled out of the seating 53.

If the second closure part 52 is in the closed position and a security seal 1 in accordance with the first exemplary embodiment is inserted into the seating 52 [53] of the first closure part 51, the two blocking tabs 21 of the security seal 1 overlap a part of the second closure part 52, as is depicted in FIG. 6B. Thus, the second closure part 52 has no play in the locked condition with respect to the second closure part 52; the security seal 1 can be designed so that the underside of the blocking tabs 21, that is, the sides of the blocking tabs 21 facing the seal base 10, are in contact with the second closure part 52.

In the present exemplary embodiment, the second closure part 52 has through-hole 54, through which the seal base 10 of the security seal 1 can be inserted and can be engaged in the slot or the seal base seating 53 of the first closure part 51 when the second closure part 52 is in the closed position of the safety closure 50. If the safety closure 50 is in the closed position and a security seal 1 is inserted into the seating 53 in the first closure part 51 of the safety closure 50, the security seal 1 creates a form closure with the closure part 52 so that the security seal 1 cannot be twisted far enough towards the safety closure 50 that the security seal 1 can be removed from the safety closure 50, as described above, i.e. by the security seal 1 being able to be twisted far enough towards the seating 53 that the locking projections 11 are essentially completely in the open sections 57. This means that, within the context of this application, the term form closure stands not only for a form closure in which no movement can take place between the components concerned, but that the movement must only be insufficient for the security seal 1 to be removed or unplugged from the seating 53.

In the present exemplary embodiment, a spacer 56 is provided on the second closure part 52. This spacer 56 fulfils two tasks. On the one hand, it produces a further form closure (in the sense defined above) between the security seal 1 and the second closure part 52; on the other hand, it protects the security seal 1 against the effect of a lateral force. Hence, the spacer 56 protects the security seal 1 from unintentional voiding and damage. With the spacer 56, two form closures are created between the security seal 1 and the safety closure 50. A first form closure is located between the lateral surface of the seal head 20 of the security seal 1 and the inner edge of the through-hole 54 and a second form closure is located between lateral surfaces of the two blocking tabs 21 and the inner edge of the recess in the spacer 56. In this exemplary embodiment, the safety closure described only serves to ensure that the safety closure 50 has not been opened as long as the security seal 1 has not been voided, i.e. the blocking tabs opposite the seal head are bent. The closure is locked using an additional conventional locking device, which is either additionally arranged on the safety closure 50 or otherwise arranged between the two closure parts, and is not further described here.

The safety closure described above can be arranged, for example, on a security container 70, which has a container tub 71 and a lid 72. Here, the first closure part 51 is arranged on the container tub 71 and the second closure part 52 is arranged on a locking tab, which is flexibly attached to the lid 72 of the security container 70. One example of this kind of security container 70 is a medical sterilization container as depicted, for example, in FIG. 7. The container in accordance with this exemplary embodiment is essentially symmetrical in design, i.e. it has a safety closure on each of its two faces. To open the container 70, i.e. to lift the lid 72 from the container tub 71, the two locking tabs which are flexibly attached to the lid 72 are pivoted so that the second closure part 52 is always moved away from the corresponding first closure part 51 with a pivoting movement. The sequence for only one side of the container, i.e. for only one safety closure, will be described in the following.

Here, the periphery of the through-hole 54 in the second closure part 52 pushes against the underside of the two blocking tabs 21. The upper surfaces of the blocking tabs 21, in turn, press against the elastic spring tabs 26 so that, on the one hand, the hinge elements 22 and, on the other hand, the elastic spring tabs 26 are bent. If the elastic spring tabs 26 are bent sufficiently, the blocking tabs 21 can bypass the free ends of the same. If the blocking tabs have bypassed the free ends of the elastic spring tabs 26, these will return to their original position. To this end, the elastic spring tabs 26 are designed so that, essentially, they do not undergo plastic deformation. The blocking tabs 21, for their part, are also bent until they have converged closely enough to pass through the through-hole 54 in the second closure part 52. The blocking tabs 21 then also return to a certain degree in the direction of their original position. The blocking tabs are prevented from returning completely to their original position, on the one hand, by the plastic deformation of the hinge elements 22, which has occurred during the bending, and, on the other hand by the elastic spring tabs 26 blocking the way.

In so doing, the safety closure 50 has been opened and, at the same time, the security seal 1 has been voided. At the same time, the security seal 1 is still in one piece, i.e. no parts of the security seal 1 have been detached or disconnected. The voiding of the security seal 1 can be very easily detected by the above-mentioned blocking tabs 21. As well, the safety closure 50 can now no longer be closed without removing the security seal 1. If an attempt is made to close the safety closure 50 without removing the voided security seal 1 from the lock 50 beforehand, the edge of the through-hole 54 in the second closure part 52 presses against the blocking tabs 21. These, however, cannot move sufficiently out of the way to enable the through-hole 54 to slide over the blocking tabs 21. These obstruct the elastic spring tabs 26 on the one hand and, on the other hand, the supporting surfaces 24. Hence, the security container 70 can no longer be closed.

The safety closure 50 and the security seal 1 also provide protection from wilful tampering. It is conceivable that someone might push the two blocking tabs 21 back after opening the catch 50, i.e. move these back on top of one another on the surface of the security seal 1 and so fix these in place. He could then move the second closure part 52 over the blocking tabs 21 and override the immobilisation of the blocking tabs 21 against each other again. Indeed, this person can close the safety closure 50 again with a great deal of effort; he cannot, however, now manage to make the security seal look as if it had never been voided. The two blocking tabs 21 still obviously project from the security seal 1. Thanks to the elastic spring tabs 26 and the plastic deformation of the hinge elements 22, they can no longer be returned to their original position.

A second exemplary embodiment of the present invention is described in the following with reference to FIGS. 8 to 14.

Figure 11:
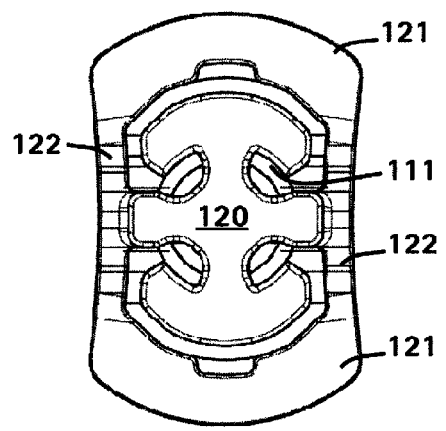
FIG. 11 shows a view of a security seal in accordance with a second exemplary embodiment of the present invention, in a non-voided state, from above.
Figure 12:
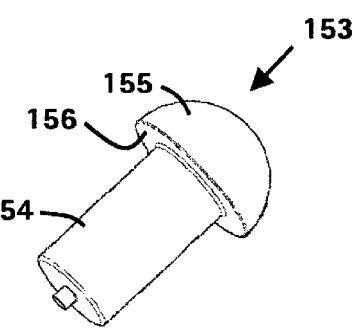
FIG. 12 shows a view of a safety closure for a security seal in accordance with the second exemplary embodiment of the present invention.
Figure 13:
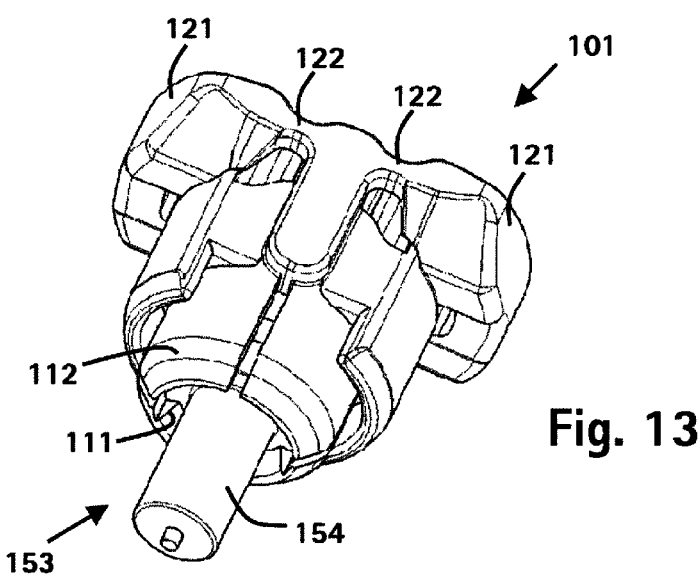
FIG. 13 shows a lateral view of a security seal, showing a safety closure in accordance with the second exemplary embodiment of the present invention.
Figure 14A:
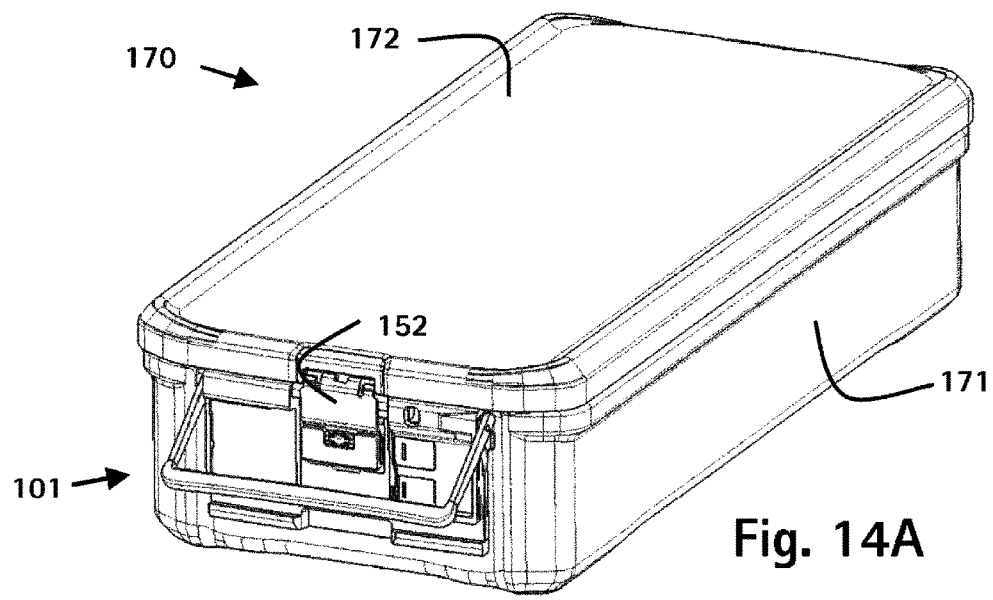
FIG. 14A shows a perspective view of a sterilization container with a safety closure and the security seal in accordance with the second exemplary embodiment of the present invention.
Figure 14B:
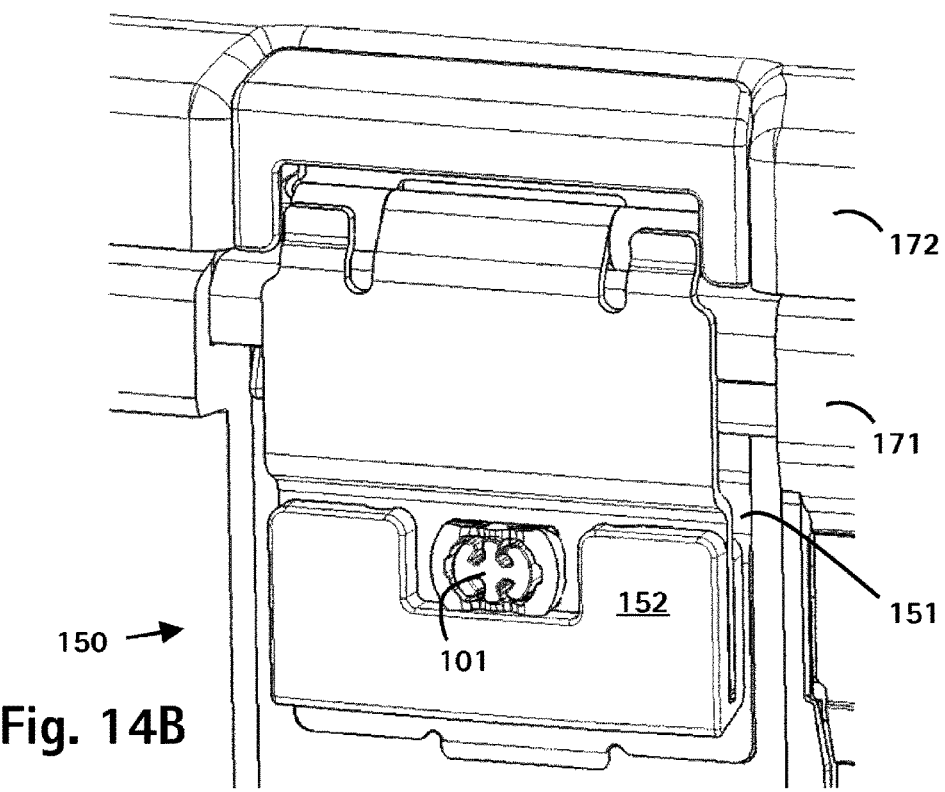
FIG. 14B shows an enlarged detail of FIG. 13A.

The security seal 101 in accordance with the second exemplary embodiment has a seal base 110 and a seal head 120. Two blocking tabs 121 are arranged on the seal head 120 similarly to the first exemplary embodiment; the cross-section of the seal head 120 of the second exemplary embodiment, however, is less rectangular. The two blocking tabs 121 are each formed with two hinge elements 122 attached to the side of the seal head 120 and movable with respect to this. The seal base 110 in this exemplary embodiment is formed with four spring tabs 112, from each of which a locking projection 111 projects radially inwards. The four spring tabs 112 together create an essentially annular cross-section and are evenly distributed around the axis of the security seal 110 [101]. The security seal 101 is also designed as one piece and formed from plastic in this exemplary embodiment. This security seal 101, however, is manufactured in an injection molding process, which manages without forced deformation. This is achieved by recesses arranged in the seal head 120 where the locking projections 111 projecting inwards are formed on the spring tabs 112 of the seal base 110, where the security seal 101 is viewed in an axial direction, so that the corresponding moldings can be removed (FIG. 11). The security seal in accordance with the second exemplary embodiment has neither elastic spring tabs 26 nor supporting surfaces 24.

In this security seal 101, it is not necessary for a type of form closure to be able to be formed between the security seal 101 and a part of the safety closure 150, with respect to rotating the security seal 101 around its longitudinal axis. This is because this security seal 101 is accommodated in a special seating 153.

As depicted in FIG. 11, the seating 153 is mushroom-shaped, i.e. it has a shaft 154 and a mushroom head 155 and thus forms an undercut surface 156. The shaft is mounted on the two closure parts 151, 152 of the safety closure 150. If the security seal 101 in accordance with the second exemplary embodiment is inserted into the seating 153, this first forces the spring tabs 112 apart since the locking projections 111 come into position and slide along this. When the locking projections 111 have passed the mushroom head 155, the spring tabs 112 return elastically into their original position and the locking projections 111 engage the undercut surface 156. To release this snap-on connection, the security seal 101 must be tilted relative to the seating 153, i.e. the longitudinal axis of the security seal 101 must adopt a certain angle to longitudinal axis of the seating 153 and the security seal 101 must be simultaneously pulled out of the seating 153.

By tilting the security seal 101 towards the seating 153, the spring tabs 112 are deformed outwards slightly, which raises the undercut of the locking projections 111 with the undercut surface 156 as far as possible and hence allows the security seal 101 to be pulled down from the seating 153.

The safety closure 150, to which this security seal 101 has been adapted, is essentially similar to the safety closure 50 for the security seal in accordance with the first exemplary embodiment. As has already been mentioned above, turning the security seal 101 around its longitudinal axis must not be restricted. Hence, the through-hole 157 in the second closure part 152 can also be circular. The diameter of the through-hole is preferably slightly greater than the largest dimension of the cross-section of the seal head 120 but less than the greatest dimension of the outer edges of the two blocking tabs 121. This will ensure an overlap between the blocking tabs 121 and the second closure part 152. Consequently, in this exemplary embodiment, it suffices if tilting the security seal 101 towards the seating 153 is prevented, so that the security seal 101 cannot be removed from the seating 153.

If the safety closure 150 is in the closed position, the security seal 101 can be inserted through the through-hole 157 in the second closure part 152 onto the seating 153, which is arranged on the first closure part 151. Here, it should be borne in mind that there is adequate space for the spring tabs 112 to be able to be deformed radially outwards. To guarantee the precise positioning of the security seal 101 along its longitudinal axis, a contact surface 158 is provided inside the seal head 120 or the seal base 110, which advantageously corresponds with the shape of the mushroom head 155. The security seal 101 can now be turned freely around its longitudinal axis without being released from the seating 153. Tilting the security seal 101 towards the seating 153 when the safety closure 150 is in the closed condition is prevented by the through-hole 157 in the second closure part 152 being sufficiently small. The narrow clearance of the undersides of the blocking elements 121 to the upper surface of the second closure part 152 also at least ensures that the security seal 101 cannot be tilted without voiding the security seal 101. This only applies in the case where there is a greater clearance between the lateral surface of the security seal 101 and the internal edge of the through-hole 157 in the second closure part 152.

If the safety closure 150 is now opened, i.e. the second closure part 152 is moved away from the first closure part 151, the blocking tabs 121, as in the first exemplary embodiment, are displaced from their original position and the hinge elements 122 are partially plastically deformed. In this exemplary embodiment, the blocking tabs 121 are not prevented from returning to their original position by elastic spring tabs. The plastic deformation of the hinge elements 122, however, ensures that the blocking tabs 121, not without force, remain in this position. Even if there are no supporting surfaces arranged on the security seal 101 in this exemplary embodiment, the blocking tabs 121 still cannot be deformed far enough in the opposite direction to allow the through-hole 157 in the second closure part 152 to be moved across the security seal 101 again. This is because of the narrow clearance between the radially internal surface of the blocking tabs 121 and the lateral surface of the seal head 120 in the area of the underside of the blocking tabs 121. Pushing the blocking tabs 121 towards the seal base 110 results in the radially internal surface of the blocking tabs 121 pressing against this lateral surface. The achievable deformation of the hinge elements 122 is so slight that the plastic deformation in the opposite direction cannot be reversed.

Even where there is intentional tampering with the security seal 101 or the safety closure 150, it is, in fact, possible to close the lock again after having opened it without removing the security seal 101, as already described for the first exemplary embodiment, but it is not possible to return the blocking elements 121 to their original position and in this way to make the voided security seal 101 appear to be a non-voided security seal 101. The blocking tabs 121 will protrude distinctly towards the seal head 120 of the security seal 101 and so will quite clearly show that the security seal 101 has been voided.

The safety closure 150 and the security seal 101 in accordance with the second exemplary embodiment can also be used for a security container such as a medical sterilization container, as depicted in FIGS. 13A and 13B [14A and 14B].

A third exemplary embodiment of the present invention is described in the following with reference to FIGS. 15 and 16.

The security seal 201 in accordance with the third exemplary embodiment features a modification of the security seal 1 in accordance with the first exemplary embodiment. Thus, only the differences from the first exemplary embodiment of the security seal are outlined in the following.

The seal base 210 is designed with two slots 213, whereby the distal end of the seal base can be deformed inwards. Thus, the seating for the seal base need not be elastically flexible in design, but the security seal 201 can be engaged in the corresponding seating by the two halves of the seal base being elastically deformed inwards until the locking projections 211 create the undercut with the corresponding area.

In accordance with this exemplary embodiment, a larger undercut can be created between the locking projections 211 and the seating. In the first exemplary embodiment without the slot 213, either the entire seal base 10, including the locking projections 11, or the margin of the seating 53 is deformed.

Figure 17:
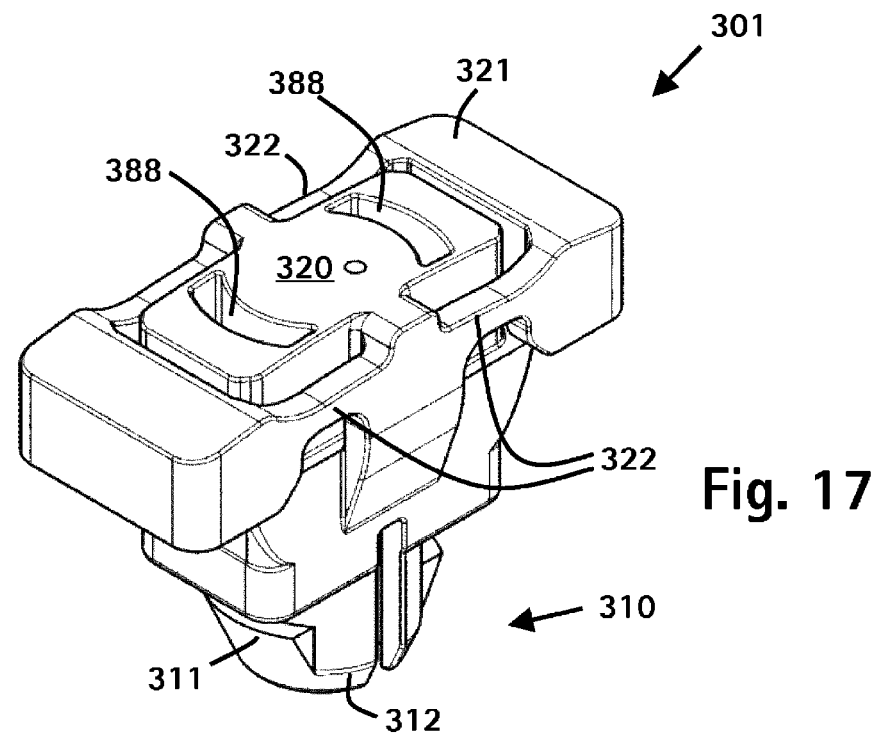
FIG. 17 shows a perspective view of a security seal in accordance with a fourth exemplary embodiment of the present invention, in a non-voided state.
Figure 18:
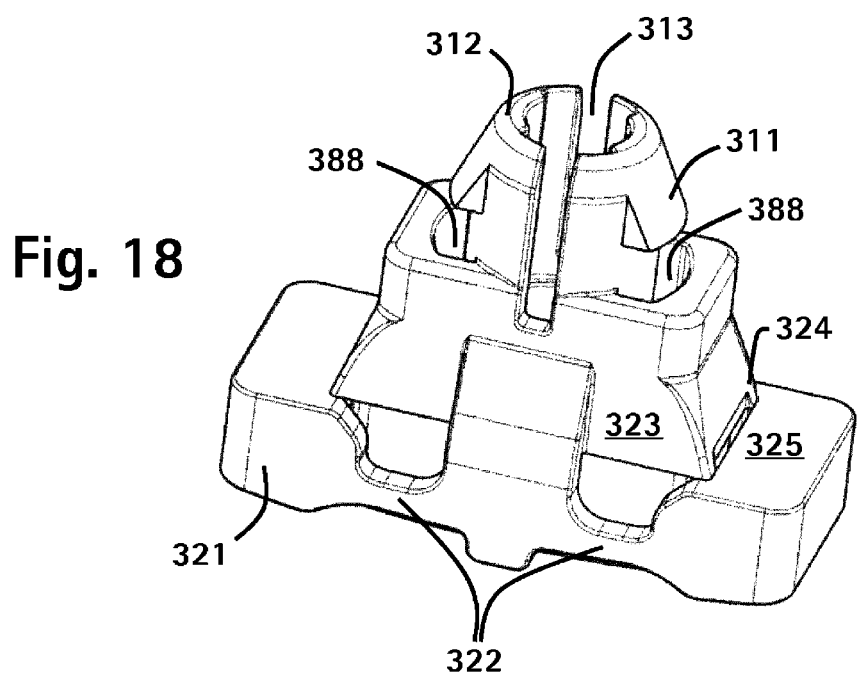
FIG. 18 shows another perspective view of a security seal in accordance with the fourth exemplary embodiment of the present invention, in a non-voided state.

A fourth exemplary embodiment of the present invention is described in the following with reference to FIGS. 17 and 18.

The security seal 201 in accordance with the fourth exemplary embodiment features a modification of the security seal 1 in accordance with the first and third exemplary embodiment. Thus, only the differences from the third exemplary embodiment of the security seal are outlined in the following.

The security seal 301 does not have elastic spring tabs on the seal head 320 to prevent the spring tabs 312 from returning to their original position if these have been deflected from their original position. In this exemplary embodiment, this is solely ensured by the plastic deformation, that is, the stress whitening, of the hinge elements 322.

In addition, through-holes 388 are arranged in the seal head 320 for a simpler design of the locking projections 311, so that parts of the mold can be inserted through here. Hence, the locking projections 311 of the security seal 301 do not have to be forcibly demolded. If the supporting surfaces 324 are also dispensed with, in principle, a production method without forced demolding can be employed.

Of course, the characteristics of the exemplary embodiments described above can also be suitably combined as required. Further embodiments will occur to the expert in the claims.

In order to detect an underhand or unauthorised exchange of security seals, these can be individualized, for example using consecutive numbering, lettering, etc.

In order to be able to indicate the voiding of the security seals more reliably, another, preferably very thin, connection can be arranged between a blocking tab and the seal head, which is destroyed on moving the blocking tabs relative to the seal head. This connection is also intended to be arranged at a distance from the hinge elements.

The invention claimed is:

1. Security seal with a seal base with at least two locking projections, and a seal head connected to the seal base with at least one blocking tab, wherein the at least two locking projections are elastically movable in a radial direction, and each blocking tab is movably connected to the seal base by at least one hinge element and wherein the at least two locking projections are arranged around the seal base at the same angular distance from one another and wherein an even number of locking projections are provided, and wherein the blocking tab has a rectangular cross-section and wherein the locking projections extend towards the seal base as the at least one blocking tab extends towards the seal head.

2. Security seal in accordance with claim 1, wherein the at least one hinge element can be at least partially plastically deformed.

3. Security seal in accordance with claim 1, which is designed as one piece, made from plastic.

4. Security seal in accordance with claim 1, with two opposing, in a radial direction, blocking tabs.

5. Security seal in accordance with clam 1, wherein each blocking tab is provided with two hinge elements, on the side of the seal head.

6. Security seal in accordance with claim 1, wherein the seal base has an essentially circular cross-section.

7. Security seal in accordance with claim 1, wherein each blocking tab projects radially at least partially towards the seal base.

8. Security seal in accordance with claim 1, wherein one of the at least one locking projection projects outwards from the seal base in a radial direction.

9. Security seal in accordance with claim 1, wherein at least one radial projection or recess is formed on the seal head or on the seal base, with which a side of the at least one blocking tab facing the seal base is in contact.

10. Security seal in accordance with claim 1, wherein at least one locking projection on the seal base is elastically mounted and projects radially inwards.

11. Security seal in accordance with claim 1 wherein one of two, four or six locking projections are provided.

12. Security seal in accordance with claim 1, wherein at least one elastic spring tab is arranged on the seal head, which projects radially over the inner edge of a blocking tab.

13. Security seal in accordance with claim 12, wherein at least one elastic spring tab is mounted on the upper surface of the seal head, centrally.

14. Security seal in accordance with claim 1, wherein at least one radially projecting locking projection is arranged on the lateral surface of the seal head and a lug is arranged on at least one blocking tab so that the lug is located opposite the at least one radially projecting locking projection and is arranged further towards the seal base in an axial direction in comparison with the at least one radially projecting locking projection.

15. Security seal in accordance with claim 14, wherein at least the lug or the at least one radially projecting locking projection is formed so as to be elastically flexible.

16. Safety closure with a first closure part and a second closure part, which can be moved back and forth between an open position and a closed position relative to the first closure part, wherein the first closure part has a seating, the seating configured to receive a seal base of a security seal in accordance with claim 1 so that, when the second closure part is in the closed position, at least one blocking tab of the security seal at least partially overlaps the second closure part on side of the second closure part opposed to the first closure part.

17. Safety closure in accordance with claim 16, wherein the second closure part has a recess and a through-hole through which the seal base can be inserted and can be engaged in the seal seating of the first closure part when the second closure part is in the closed position.

18. Safety closure in accordance with claim 16, wherein the seal base of the security seal can be engaged in the seal seating of the first closure part when the second closure part is in the closed position so that the security seal is interlocked with the second closure part so that the security seal opposite the first closure part is essentially held immovably, in particular, cannot be turned, tilted and/or shifted, while the security seal can be moved towards the first closure part when the second closure part is in the open position, in particular, turned, tilted and shifted.

19. Safety closure in accordance with claim 16, wherein a seating on the first closure part has at least one recess, with an essentially rotationally symmetrical section, with at least one radial outward widening, into which the seal base of a security seal can be inserted.

20. Safety closure in accordance with claim 16, wherein the seating on the first closure part is an essentially circular recess with at least one radial outward and inward widening, into which the least one locking projection can be inserted.

21. Safety closure in accordance with claim 16, wherein a seating on the first closure part is a mushroom-shaped projection, on which the seal base of a security seal can be placed.

22. Safety closure in accordance with claim 16, which has at least one of a snap-in mechanism, with which the second closure part can be locked on to the first closure part.

23. Security container according to claim 16, including a container tub, a lid and a safety closure, wherein either the first or the second closure part is arranged on either the container tub or the lid respectively.

24. Security container in accordance with claim 23, wherein at least the first closure part or the second closure part is arranged on a locking tab, which is correspondingly arranged on the container tub and the lid so as to be able to pivot.

25. Sterilization container with a container tub with at least a first closure part, which has a recess with two opposing curved contact surfaces formed on two curved sections, so that the recess is aligned to receive a seal base of a security seal, the recess has an essentially circular cross-section and two locking projections projecting radially outwards and which can be inserted into the recess in an axial direction so that the locking projections create a locking undercut with the curved sections and a lateral surface of the seal base is partially seated on a contact surface and is also aligned so that a snap-on connection between the locking projections and the curved sections can be lifted off by turning the security seal around its longitudinal axis through roughly 90°, so that the security seal can be removed from the recess, and a container lid, which has at least one locking tab, which is swivel-mounted to the container lid so that it can be moved back and forth from an open position to a closed position, and a second closure part, which has a through-hole, which has an essentially non-rotationally symmetrical cross-section and is aligned to interlock with a seal head of the security seal in the direction of rotation so that moving the locking tab in the direction of the open position relative to the security seal results in at least one blocking tab arranged on the seal head of the security seal being positioned on at least one part of an edge of the through-hole and continued movement of the blocking tab in one direction results in at least partial plastic deformation of the at least one blocking tab so that the through-hole of the locking tab can be guided over the seal head.

26. Sterilization container in accordance with claim 25, wherein an additional locking or closure mechanism is arranged between the locking tab and the first closure part so that the safety closure is not retained when the locking tab is in the closed position.

* * * * *